(12) United States Patent
Jensen et al.

(10) Patent No.: US 6,739,340 B1
(45) Date of Patent: May 25, 2004

(54) DEVICE FOR PREVENTION OF INVOLUNTARY URINATION

(75) Inventors: Hanne Jensen, Koebenhavn (DK); Karina Markersen, Gentofte (DK); Allan Tanghoej, Kokkedal (DK); Anna Mortensen, Kokkedal (DK); Jan Torstensen, Virum (DK); Henrik Lindenskov Nielsen, Smoerum (DK); Marianne Saaby Ringaard, Gentofte (DK); Birgitte Baht, Klampenborg (DK); Suzanne Eis Benzon, Fredensborg (DK)

(73) Assignee: Codan Steritex ApS, Espergaerde (DK)

( * ) Notice: Subject to any disclaimer, the term of this patent is extended or adjusted under 35 U.S.C. 154(b) by 0 days.

(21) Appl. No.: 09/423,290
(22) PCT Filed: May 4, 1998
(86) PCT No.: PCT/DK98/00173
§ 371 (c)(1),
(2), (4) Date: Jan. 12, 2000
(87) PCT Pub. No.: WO98/49980
PCT Pub. Date: Nov. 12, 1998

(30) Foreign Application Priority Data

| May 6, 1997 | (DK) | 0525/97 |
| Jul. 11, 1997 | (DK) | 0851/97 |
| Jan. 7, 1998 | (DK) | 0014/98 |

(51) Int. Cl.$^7$ .................................................. A61F 5/48
(52) U.S. Cl. ............................... 128/885; 128/DIG. 25
(58) Field of Search .................................. 128/885, 886, 128/DIG. 25; 600/29–31

(56) References Cited

U.S. PATENT DOCUMENTS

| 3,404,682 A | | 10/1968 | Waldron ...................... 128/285 |
| 3,590,816 A | * | 7/1971 | Rosenthal .................... 128/840 |
| 4,019,498 A | * | 4/1977 | Hawtrey .............. 128/DIG. 25 |
| 5,036,867 A | | 8/1991 | Biswas ........................ 128/885 |
| 5,417,226 A | * | 5/1995 | Juma ........................... 128/885 |
| 5,671,755 A | * | 9/1997 | Simon ......................... 128/885 |

FOREIGN PATENT DOCUMENTS

| EP | 0 263 466 | 4/1988 |
| EP | 0 264 258 | 4/1988 |
| EP | 0 363 421 | 4/1990 |
| WO | WO88/10106 | 12/1988 |
| WO | WO89/09582 | 10/1989 |
| WO | WO95/05790 | 3/1995 |

* cited by examiner

Primary Examiner—Michael A. Brown
(74) Attorney, Agent, or Firm—Jacobson Holman PLLC (57) ABSTRACT

The device comprises a body for arrangement in the vagina for compressive action on and support of the neck of the bladder and optionally the urethra. The body has a substantially elongated shape with a longitudinal axis extending, in the intended direction of insertion, from a proximal to a distal end, and is made from a compressive and elastically deformable material. The body comprises at least one part protruding from the outer surface of the body and providing at least one pressure area for contact with the neck of the bladder and optionally the urethra.

35 Claims, 4 Drawing Sheets

DEVICE FOR PREVENTION OF INVOLUNTARY URINATION

BACKGROUND OF THE INVENTION

1. Field of the Invention

The present invention relates to devices for prevention of involuntary urination, in particular devices comprising a body for arrangement in the vagina for compressive action on and support of the neck of the bladder, combinations of such devices and applicators for use in insertion of the devices into the vagina and methods of manufacturing such devices.

2. Description of the Related Art

The present invention relates to a device for prevention of involuntary urination in a female, comprising a body for arrangement in the vagina for compressive action on and support of the neck of the bladder and optionally the urethra, in which the body has a substantially elongated shape with a longitudinal axis extending, in the intended direction of insertion, from a proximal to a distal end, and in which the body is made from a compressive and elastically deformable material.

Stress incontinence is a nuisance experienced by up to a third of all women at some time or other during their lives.

Stress incontinence is often due to hypermobility of the bladder neck because of insufficient support thereof. Treatments of stress incontinence are aimed at improving the closure of the urethra by better support of the pelvis.

Severe cases of stress incontinence are normally relieved by surgical intervention, while less severe cases of stress incontinence can often be fully or partially relieved by training or retraining of the pelvic musculature.

Training or retraining of a pelvic muscle may, however, extend over many months, and as mentioned, may not in all cases relieve the problem completely.

Thus, there is still a need to find a product which can relieve stress incontinence. The use of sanitary towels and napkins for relieving the inconveniences connected with involuntary urination is generally known. This, however, is a method associated with great disadvantages for the woman, as the sanitary towels are unhandy and voluminous, among other things.

Furthermore, it is known that stress incontinence may be relieved by the use of a tampon-like device which is arranged in the vagina for compressive action and support of the neck of the bladder.

Such a device for relief of stress incontinence is discussed in, for example, U.S. Pat. No. 4,019,498. This device consists of a body of compressible elastic material in the form of a mushroom which is compressed and then placed in a bag. The bag with the body is inserted in the vagina, whereupon the bag is punctured. The body will then press against the neck of the bladder and support this. This method partly involves a cost-increasing component—the bag—and partly there is a risk of damaging the vagina and adjacent tissue when puncturing the bag. The device excerts sufficient pressure on the anterior wall of the vagina to close the urethra and the woman has to remove the device when she has to urinate. Removing of the device is facilitated by the stem portion of the mushroom which is projecting toward the vagina opening.

Furthermore, it is impossible or difficult to adjust the position of the body after the placing in the vagina. Additionally, the body acts purely by the compressibility of the material, for which reason it is necessary to manufacture it in several sizes.

EP-A-363421 also describes a device for arrangement in a woman's vagina with the object of relieving incontinence. This device also has the disadvantage that it acts as a support of the bladder neck merely in consequence of the compression taking place depending on the size of the vagina and the size of the body. It is therefore also in this case necessary to manufacture different sizes to compensate for the different vaginal diameter.

Still further, EP-A-264258 describes an incontinence device—specifically for use in vaginal and rectal prolapse—designed as a U-shaped body, which acts by lifting the neck of the bladder, as, after being arranged, the body returns to its rest position, and one leg of the U bears against the bladder neck of the bladder, which is lifted, whereby continence is obtained. This is thus a relatively rigid structure which is also designed in rather large dimensions.

This device, as well, is required to be manufactured in several different sizes to compensate for the different vaginal diameters, as its lift is exclusively due to its shape, just as it is uncomfortable to wear owing to its rigid and fairly large structure.

A common feature of the above incontinence products is thus that it is necessary to manufacture the product in many different sizes to compensate for the various vaginal diameters.

This is partly economically inappropriate and partly the body will not have an optimum function even after careful selection of size according to a woman's vaginal diameter, as the support by the bodies of the bladder neck will vary according to the physical posture of the woman and the state of tension of her pelvic muscle. There is thus a great risk that by use of the above mentioned devices, the woman will suffer from involuntary urination, and/or that the device will cause inconvenience, cause pain or even damage the vaginal mucous membrane when the woman is in physical movement or tightens her pelvic musculature.

Thus, the above-mentioned devices are economically unsuitable, just as they do not have an optimum function throughout their service life.

Published international application No. WO95/05790 discloses a device having a body comprising two or more legs which are joined in a flexible base. The body of the device is inserted into the vagina in an elastically deformed state with the legs bent in a direction towards each other. Due to the compressive and elastic properties of the body in combination with its properties of restitution deriving from the deformation of the legs, the device will provide support for the bladder neck without blocking the urethra for varying spatial conditions in the vagina.

Although this known device alleviates the drawbacks of the above-mentioned devices, it still has rather large dimensions and furthermore, the two-legged design has a risk of improper placement during insertion.

It is the object of the present invention to provide an improved device of the kind mentioned in the introduction, which comfortably relieves the nuisances indicated and thus secure the woman an optimum support regardless of her physical condition and which is at the same time easy to handle. Just as important, the woman shall be able to urinate normally without having to remove the device. Eventually, the device should be easy to manufacture.

BRIEF DESCRIPTION OF THE INVENTION

The present invention relates, in its broadest aspect, to a device for prevention of involuntary urination in a female, comprising a body for arrangement in the vagina for compressive action on and support of the neck of the bladder and optionally the urethra, in which the body has a substantially elongated shape with a longitudinal axis extending, in the intended direction of insertion, from a proximal to a distal end, and in which the body is made from a compressive and elastically deformable material, said device being characteristic in that the body comprises at least one part protruding from the outer surface of the body and providing at least one pressure area for contact with the neck of the bladder and optionally the urethra and in that the body is provided with at least one string extending from the distal end.

The protruding part(s) ensure a higher pressure during movements and thereby a better support of the neck of the bladder. The device seems relatively small and appealing to the user although it performs the same pressure as larger and already known products. Also it assures that no involuntary urination will occur while at the same time voluntary urination is possible.

The device according to the invention for prevention of involuntary urination in a female may be symmetric with respect to the longitudinal axis of the body, preferably axisymmetric. Symmetric and in particularly axisymmetric products have the advantage that the body need not be oriented at insertion. Additionally, symmetric products are generally easier and cheaper to manufacture and therefore economically appropriate, especially for disposable products.

The protruding part or parts may in an embodiment protrude from the body circumferentially, substantially perpendicular to the longitudinal axis of the body. It is difficult to define the size and height of the protruding part(s) as these measures depend on the chosen material but the protruding part(s) has to be so elevated above the adjecent lower parts and has to cover an area adequatly big in order to produce an increased pressure against the bladder neck. The pressure should be increased when compared to the pressure performed by a cylindric body with a diameter equal to the cross section in the lower adjecent part(s). On the other hand the area covered by the protruding part(s) can not be to big as this will increase the material consumption, affect the user-appeal of the product and could possibly spoil the ability to urinate voluntarily.

Exactly how elevated and how big a certain area of a protruding part should be depends mainly on the elasticity of the chosen material.

How far away the protruding part(s) should be placed from each other also partly depends on the material but as a guideline the adjecent low areas should have a width of at least 3 mm preferably of at least 5 mm measured halfway between the top of a protruding part and the bottom of a low adjecent part.

In order to facilitate removal of the device after use, the body is provided with at least one string projecting from the distal end of the body.

In a further development of this embodiment, there are two or more, e.g. three, protruding parts with adjecent low part(s) formed as a narrowed waist(s) between them.

In another embodiment, there are at least two protruding parts extending substantially parallel to the longitudinal direction of the body. The adjecent low area between the longitudinally protruding parts makes a "cradle" which fits the neck of the bladder not only at the bottom, but also along the sides and provides an optimum support.

The body may have a substantially conical or frustoconical shape, which provides for a reliable support of the neck of the bladder and possibly the urethra. The base of the cone or the frustum may correspond to the distal end of the body, i.e. the end facing outwards in the position of use, which facilitates insertion of the device. In a preferred embodiment, however, the base of the conical or frustoconical body corresponds to the proximal end thereof. By this design, forces acting on the device due to sudden movements of the user, such as sneezing, coughing and jumping, will be transferred into one transverse and one longitudinal component. The latter component will prevent the device from being pressed out of the vagina.

The body of the device may be formed in a traditional, hydrophilic material, such as polyurethane or polyvinyl alcohol, in which case the device has to be wetted before use, but in a preferred embodiment the body is formed in a hydrophobic material, preferably hydrophobic polyurethane. The use of a hydrophobic material instead of a hydrophilic material that needs to be soaked in water or the like before use has the advantage that the woman is free to apply the device any place she wants without the need of water. Further it reduces the risk of infection caused by water of poor quality.

The material is preferably porous.

In a further aspect the invention relates to the combination of a device for prevention of involuntary urination in a female and an applicator for use in the insertion thereof into the vagina.

The applicator is characteristic in that it comprises an elongated member for abutment with at least the distal end of the body of the device during the insertion. The elongated member of the applicator will protrude from the vagina during the insertion and secures that a reliable positioning of the device may take place with minimum manual contact with the device.

Also the employment of the applicator reduce the circumference of the device at the time of insertion which make the device even more appealing to the female users. Normally the maximum sectional area of the body will be reduced by at least 50% when the applicator is employed.

In its simplest form, the applicator comprises one substantially rod-shaped end portion for abutment with an indentation in the distal end of the body of the device.

In order to indicate the correct depth of introduction, the applicator may at the other end portion comprise marks.

In a preferred embodiment, the elongated member of the applicator comprises a piston-like element, which fits into a substantially tubular part.

The tubular part may be open at both ends and define a cavity for accommodating the device in a compressed and elastically deformed state.

Alternatively, the elongated member of the applicator comprises a tubular part and accommodates the device in a compressed and elastically deformed state.

In the case of devices made from a hydrophobic material, which do not have to be soaked before use, the preferred combination of a device and an applicator comprising at least one tubular part for accommodating the body of the device in a compressed and elastically deformed state is particularly advantageous, as the device and the applicator may be delivered as a ready-to-use unit, e.g. in hygienic one-piece packagings.

Still further the invention relates to a method of manufacturing a device for prevention of involuntary urination in a female.

The method comprises the steps of mixing the components of the material, injecting the material into a mould, optionally accelerated hardening by heating the mould, and removing the body from the mould.

At some stage of the manufacturing process, at least one string is fastened to the body.

In a preferred embodiment, the string is fastened to at least one portion of the mould prior to the injection of the material into the mould. This provides for an easier and cheaper production in comparison with traditional methods, in which the string has to be sewn into the body of the device after the removal of the body from the mould, which is a time-consuming operation.

BRIEF DESCRIPTION OF THE DRAWINGS

Below embodiments of a device for prevention of involuntary urination in a female and the combination of a device and an applicator according to the invention will be explained in more detail with reference to the drawings, in which.

DETAILED DESCRIPTION OF THE INVENTION

In a first aspect, the invention relates to a device for prevention of involuntary urination in a female, comprising a body 1, 11, 21, 31, 41, 51 for arrangement in the vagina for compressive action on and support of the neck of the bladder and optionally the urethra. The body 1, 11, 21, 31, 41, 51 comprises at least one part 5, 15, 25, 26, 35a, 35b, 45, 46a, 46b, 55a, 55b protruding from the outside of the body and providing an increased amount of pressure. All of the devices of the described embodiments have a body which is symmetric with respect to a longitudinal axis of the body, preferably axisymmetric. Furthermore, the body is substantially conical or frusto-conical.

In the embodiments of FIGS. 1 to 3 and 5, the parts 5, 15, 25, 26, 45, 46a, 46b protruding from the outside of the device are provided around the device like an enlarged diameter and are essentially perpendicular to the longitudinal axis of the device.

Figure 1:
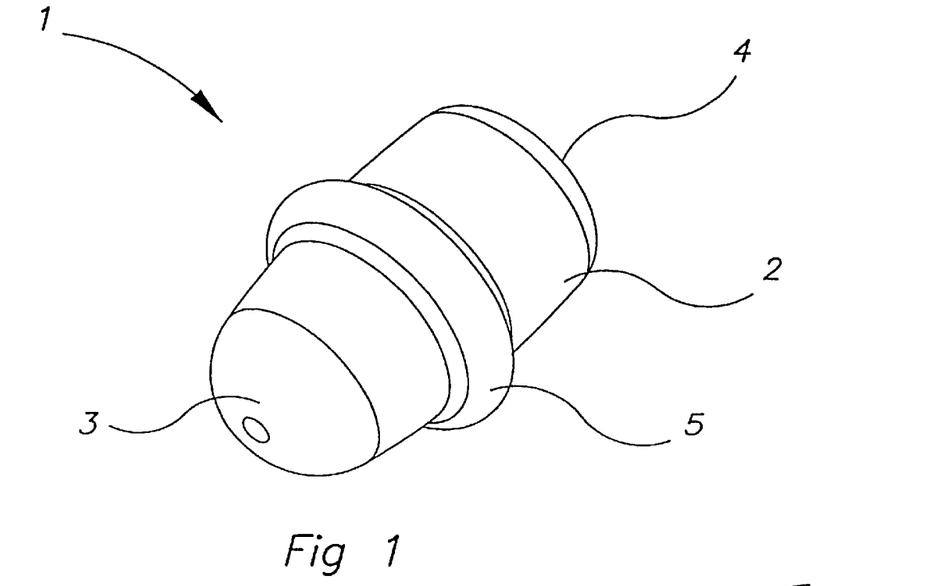
FIG. 1 illustrates a device according to a first embodiment of the invention.

In FIG. 1 the body 1 has an essentially tampon-like basis 2, where the proximal or top end 3 has a smaller diameter than the distal or bottom end 4. The basis 2 is further provided with an enlarged diameter in an area in the form of the protruding part 5 around the middle. The bottom end 4 may further be provided with a not shown indentation for co-operation with an applicator.

Finally, a not shown string may be fastened, e.g. sewn into the bottom end 4 of the body 1 in order to facilitate insertion of the body into the vagina in connection with the use of an applicator and in order to facilitate removal of the body from the vagina.

Figure 2:
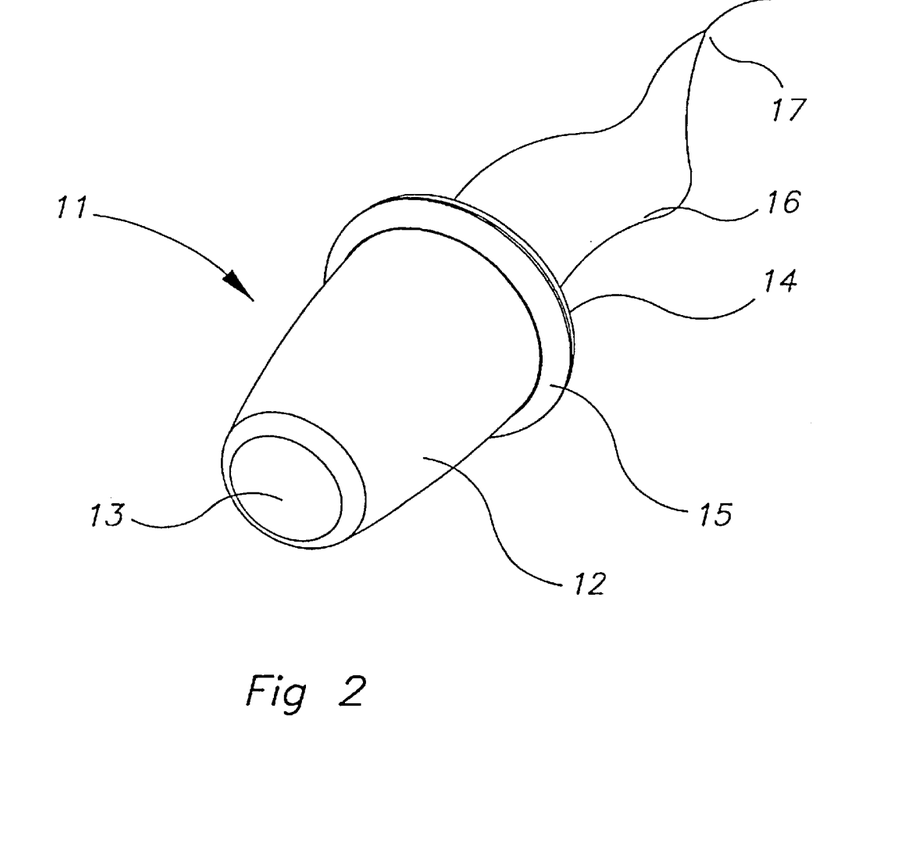
FIG. 2 illustrates a device according to a second embodiment of the invention.

In the FIG. 2 embodiment the body 11 has an essentially tampon-like basis 12, where the proximal or top end 13 has a smaller diameter than the distal or bottom end 14. The basis 12 is further provided with an enlarged diameter in an area corresponding to the protruding part 15 next to the bottom end 14. The bottom end may further be provided with a not shown indentation for cooperation with an applicator. Finally a string 16, 17 may be secured into the bottom end 14 of the body 11 in order to facilitate the insertion of the body into the vagina in connection with the use of an applicator-and in order to facilitate removal of the body from the vagina.

Figure 3:
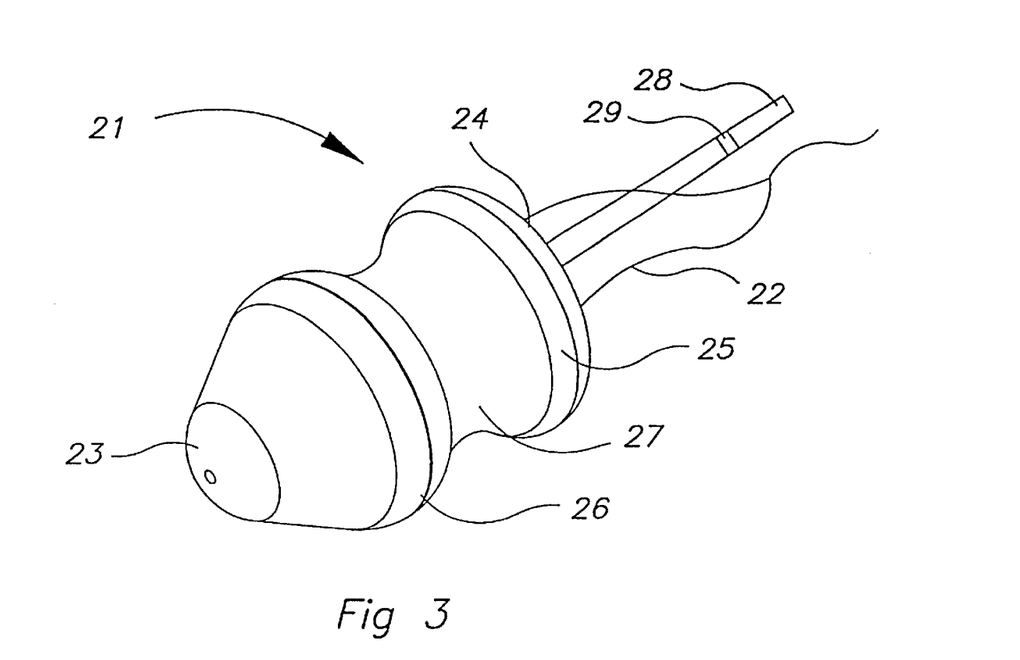
FIG. 3 illustrates the combination of a device according to a third embodiment of the invention and an applicator.
Figure 5:
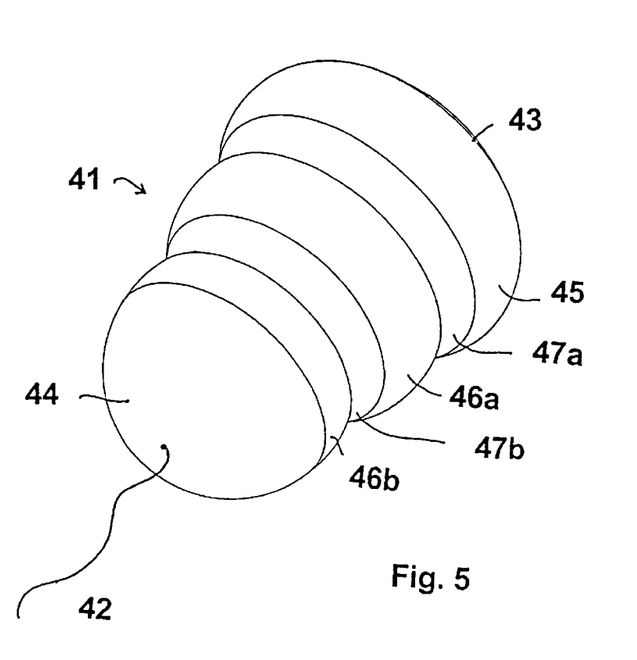
FIG. 5 illustrates a device according to a fifth embodiment of the invention.

In the embodiments of FIGS. 3 and 5, the body is provided with at least two protruding parts 25, 26, 45, 46a, 46b, with an adjacent low area shaped as a narrowed waist part 27, 47a, 47b between them.

In the embodiment shown in FIG. 3 the body 21 comprises a proximal or top end 23, a distal or bottom end 24, two areas with enlarged diameters in the form of the protruding parts 25 and 26 and adjacent low area waist part 27 in between the enlarged diameters. The body 21 is further provided with a not shown indentation. An applicator 28 is placed in that indentation with one end portion. At the opposite end portion the applicator 28 comprises marks 29 for showing the right introduction depth of the body. The applicator may be made of any suitable material, e.g. plastic or paper. The body 21 Is further provided with a string 22.

In the FIG. 5 embodiment, the body 41 is provided with enlarged diameters in the areas defined by the three protruding parts 45, 46a, 46b with the adjacent low areas shaped as narrowed waists 47a, 47b between the parts 45, 46a and 46a, 46b, respectively. The proximal or top end 43 has a larger diameter than the distal or bottom end 44, from which a string 42 protrudes.

Figure 4:
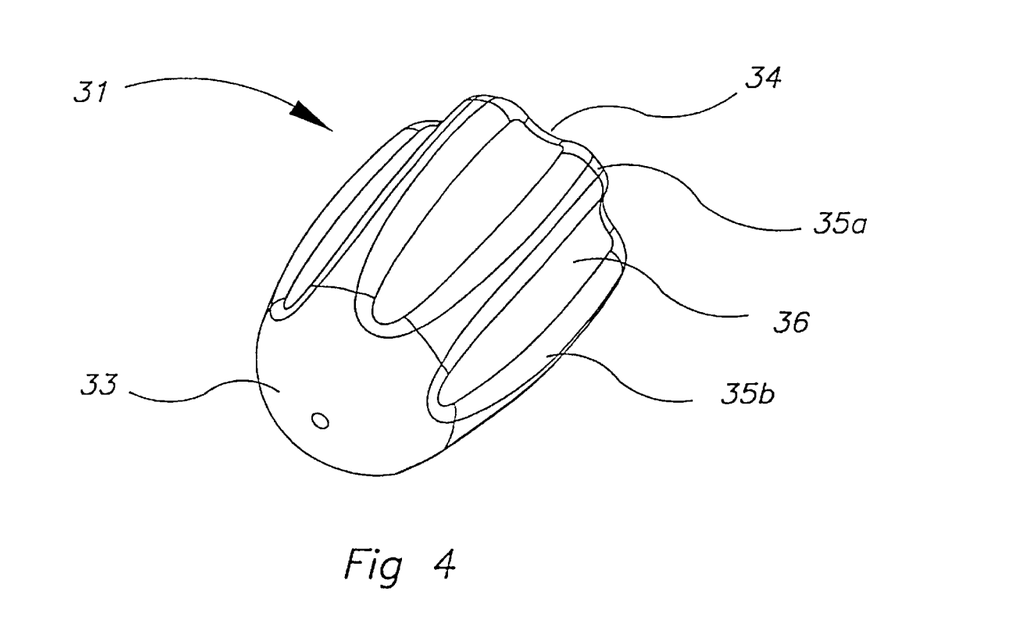
FIG. 4 illustrates a device according to a fourth embodiment of the invention.
Figure 6:
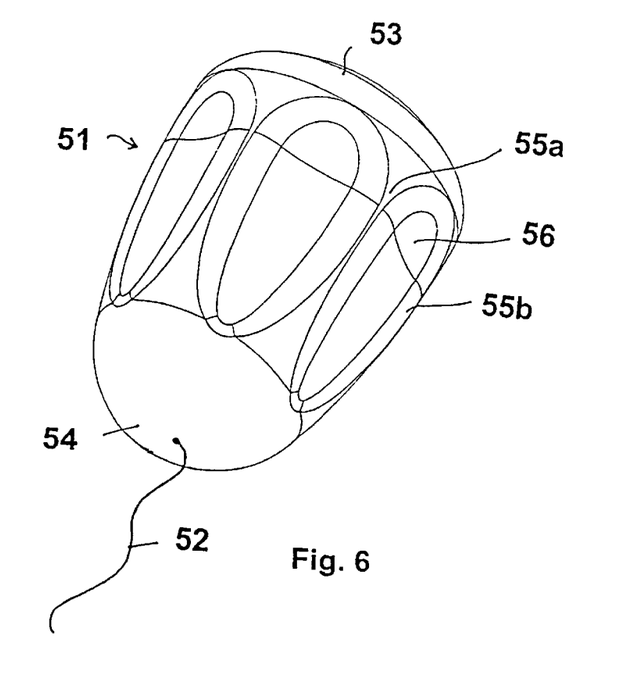
FIG. 6 illustrates a device according to a sixth embodiment of the invention.

In the embodiments of FIGS. 4 and 6, the device for prevention of involuntary urination according to the invention is provided with at least two parts 35a, 35b, 55a, 55b essentially parallel to the longitudinal axis of the body 31, 51.

As shown in FIG. 4 the body 31 comprises a proximal or top end 33 and a distal or bottom end 34. Parallel to the longitudinal axis there is provided six longitudinal protruding parts 35a, 35b with adjacent low areas 36 in between. This embodiment may be provided with a not shown indentation for the not shown applicator as well as a not shown string that may be sewn into the bottom end 34 or moulded into the body 31.

Similarly, the device in the FIG. 6 embodiment has six parts 55a, 55b protruding from the body 51. The difference from the embodiment of FIG. 4 is that the proximal or top end 53 has a slightly larger diameter than the distal or bottom end 54, from which a string 52 projects.

It should be noted that the number of protruding parts may vary considerably, from two parts and up to eight or ten.

In the case of hydrophilic devices suitable materials for forming the device are preferably formalized polyvinyl alcohol and polyurethane.

According to the invention, the preferred materials for forming the device are hydrophobic polyurethane, and most preferably the hydrophobic polyurethane is based on a hydrophobic polyol with a functionality of at least two, but other materials may also be applied. Preferably the material is a porous material.

Generally a suitable material may be prepared by mixing a hydrophobic polyol with an isocyanate and by adding a blowing agent. E.g. a suitable polyurethane material may be prepared by mixing a prepolymerized polyurethane with water, where 0.5–3%, preferably 1–2% of a surface active agent and 0.1–2%, preferably 0.3–1% of a catalyst has been added to the aqueous phase. The polyurethane may be Suprasec X2700 from ICI. The mixing ratio between the polyurethane component and the aqueous phase is selected so that there is an excess of water. This material will not absorb liquid water and it is a compressible, resilient material.

The isocyanate may be based on MDI, TDI or mixtures thereof.

The polyol and the isocyanate may be prepolymerized.

A suitable catalyst are chosen from the groups of organic bases and organome tallic compounds with thorough considerations about toxicity.

As blowing agent can either be used chemical blowing agents such as pentane or other CFC-replacements.

Generally additives such as surface active agents, catalysts, chain extenders or crosslinkers may be added to either the waterphase in prepolymer systems, or to the polyolphase.

The surface friction of the product may be lowered by adding surface active agents or oils.

The body may additionally be coated fully or partially with an elastic polymer film such as polyethylene, polypropylene or polyvinylchloride.

A suitable foam may be produced by mixing the polyol with additives and a catalyst, adding the isocyanate and the blowing agent. The polyol and the isocyanate may be prepolymerized and in that case the additives are added to the waterphase before mixing it with the prepolymer.

For reasons which will be explained in the following, the material should possess the capability of being stored in a compressed and elastically deformed state for even long times, and subsequently be able to expand and substantially regain its original shape.

In a second aspect, the invention relates to a combination of a device according to the invention with an applicator 28, 29 for use in the insertion thereof into the vagina. In the embodiments of FIGS. 1 to 4 the body 1, 11, 21, 31 is provided with an indentation in its bottom end 4, 14, 24, 34 and the applicator 28 comprises an elongated member with an end portion for abutment with said indentation for arrangement of the body 1, 11, 21, 31 in the vagina.

Figure 7:
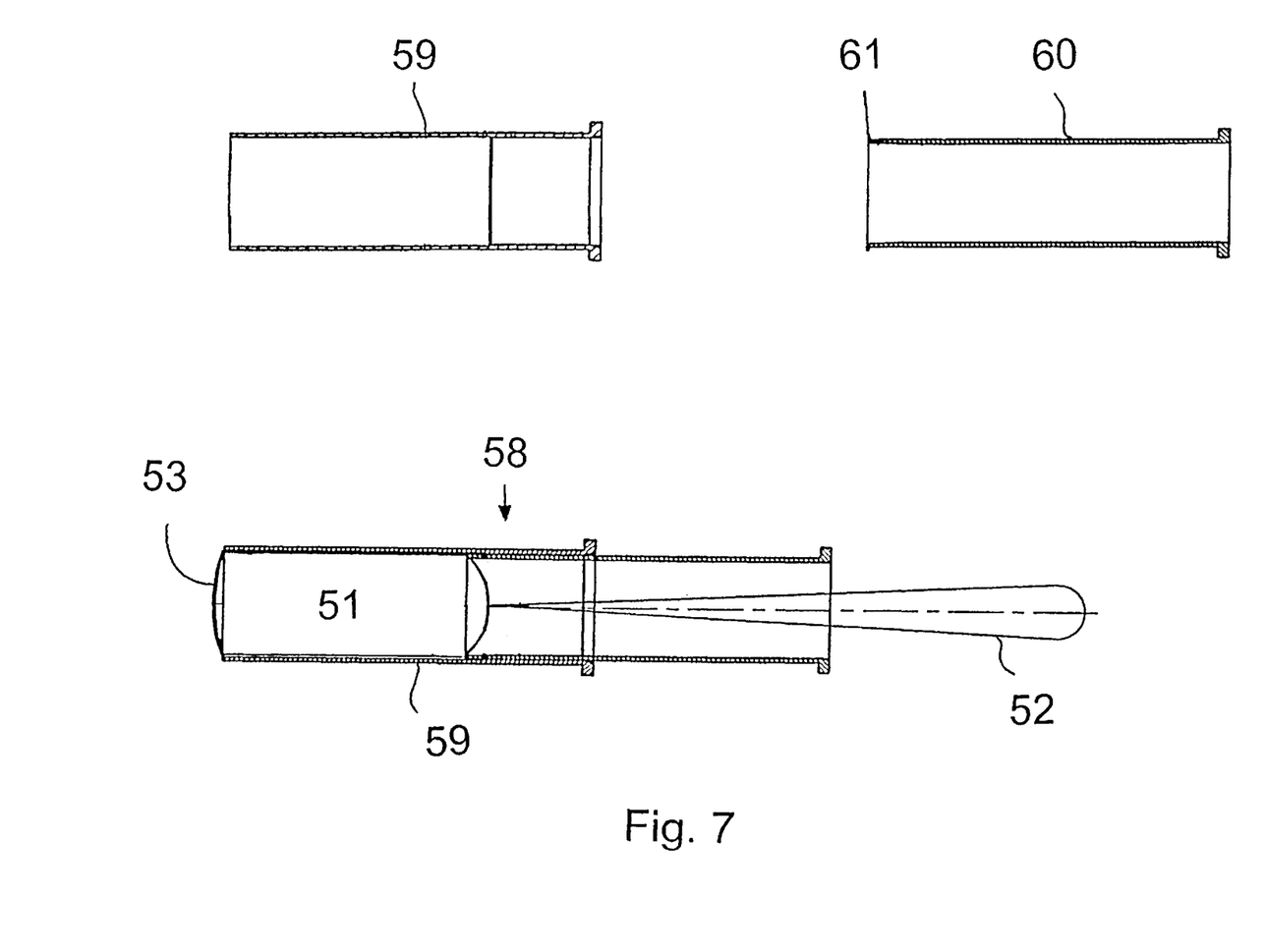
FIG. 7 illustrates the combination of a device and an applicator according to the invention.

In FIG. 7 an alternative embodiment of an applicator 58 is shown in combination with a device as shown in FIGS. 1–6. It should be noted that these applicators would perform equally well with any of the devices shown in FIGS. 1 to 6, although they are particularly advantageous in the case of conical or frusto-conical devices having a proximal or top end with larger dimensions than the distal or bottom end as is the case with the embodiments of FIGS. 5 and 6.

In FIG. 7, the body of the device 51 is received in a substantially tubular part 59, which is open at both ends, so that only its top end 53 and the string 52 may be seen. An elongated member 60 of the applicator comprises at its upper end a piston-like element, which e.g. may be constituted by the rim 61 of the likewise tubular elongated member. The elongated member 60 and thus the piston-like element 61 fits into the tubular part 59. When inserting the device, the applicator is placed such that the tubular part 59 is arranged in the vagina, following which a pressure is exerted on the elongated member, whereby the device is ejected. The body of the device will seek back to its state of rest from the compressed and elastically deformed state when assuming its position supporting the neck of the bladder and/or the urethra. The applicator may now be pulled out, leaving the device in its position of use.

Alternatively, the applicator may be of a more compact design. In this design the elongated member of the applicator comprises an internal tubular part, of which only a distal end section may be seen, and which accommodates the device in the shown state. The internal tubular part fits into an external, substantially tubular part corresponding to the tubular part 59 of the FIG. 7 embodiment. In order to prepare the applicator for insertion, the internal tubular part is withdrawn from the external tubular part by a pull in the distal end section of the inner tubular part. During this movement, the device substantially maintains its position, e.g. in that holding means are provided at the proximal end section of the external tubular part for holding the top end of the body of the device. The compressed and elastically deformed body of the device expands slightly during this movement. When the internal tubular part has been withdrawn sufficiently, e.g. to a position, in which the applicator assumes a position substantially corresponding to the position shown in the FIG. 7 embodiment, and the proximal end of the internal tube abuts the distal or bottom end of the body of the device, the internal tubular part is moved in the direction of insertion, whereby the device is ejected as described in the afore-going.

In a third aspect, the invention relates to a method of manufacturing a device for prevention of involuntary urination in a female, comprising a body for arrangement in the vagina for compressive action on and support of the neck of the bladder and optionally the urethra. The method comprises the steps of mixing the components of the material as stated above, injecting it into a corresponding mould, optionally accelerated hardening by heating the mould, and removing the body from the mould. Subsequently, the body may optionally undergo washing and drying, and optionally fastening a string to the body. The fastening of the string may be done by sewing, gluing, welding etc., or, as is preferred, in that a string is fastened to at least the portion of the mould corresponding to the proximal or upper end of the body prior to the injection of the material into the mould and in such a way that the string extends substantially along the intended longitudinal axis of the body, e.g. by fastening the string at the mould portion corresponding to the bottom or distal end of the body as well. After the hardening stage, the device may be pulled out of the mould by means of the string, which thus extends from the top end to the bottom end, from it projects. At the top end, any excessive string material may be cut off, following which the material closes again by itself, the string is retained safely in the body.

Eventually, the device may be placed in an applicator and packed.

Experimental Part

EXAMPLE 1

Preparation of a device of the invention according to FIG. 3,

A product with a reel-shaped symmetric body 21, with a larger diameter 26 in the top end 23 and bottom end 24 and a smaller diameter 27 in the middle and an indentation in the bottom end 24, where an applicator 28 can be fitted into in order to ensure optimal security during application was produced in a PU-foam using a prepolymeric system Suprasec X2700 from ICI.

An aqueous phase containing a surface active additive Emulgade F from Henkel and a catalyst Dabco T from Air Products was mixed into the prepolymer as stated above. The mixture was immediately injected into a corresponding aluminium mould. The mould was closed and placed in an oven at 50 C for three minutes.

Burrs were removed and the body was washed and dried to remove any low molecular substances. Further a string was sewn into the body in order to facilitate insertion of the body into the vagina in connection with the use of an applicator and in order facilitate removal of the body 21 from the vagina, the device may finally be packed and sterilised.

The PU-foam is hydrophobic and will not absorb liquid water or secretions from the vagina.

The larger diameter of the product produced according to this Example 1 is about 33 mm and the smaller diameter is about 23 mm. The length is 51 mm.

Use of the Device Prepared According to Example 1

The applicator 28 was placed in the corresponding indentation in the bottom end 24 of the body 21 and by placing the body in the applicator the maximum sectional area was reduced by approximately 63%. The applicator 28 was then inserted into the vagina together with the body 21 as far as the marks 29 on the applicator 28, with the string 22 hanging out of the vagina. The applicator 28 was then removed. During use, ultrasonic scanning was carried out. The scanning showed that the device supports the neck of the bladder during strains such as cough, sneeze and jumps.

After use of the device the body 21 was easily removed by pulling gently in the string 22. During use the woman urinated voluntarily without problems.

EXAMPLE 2

Alternative preparation of a device of the invention according to FIG. 3.

The device according to FIG. 3 could alternatively be prepared by using a polyurethane system Elastofoam from BASF.

To part A (polyol 310/043) with catalyst and additives was added 1% of a silicone surface active agent Niax from OSI Specialities, the polyol was mixed with part B (MDI 130). The mixture was immediately injected into a corresponding aluminium mould. The mould was closed and placed in an oven at 50 C for 3 minutes.

The device was then finished and used as described in example 1.

EXAMPLE 3

Preparation of a device of the invention according to FIG. 4.

A product with an essentially parabolic shape with six longitudinal protruding parts was produced and used in the same way as Example 1. In order to avoid problems while positioning the body the protruding parts were provided symmetrically on the body. The larger diameter of the product according to this example is 35 mm and the smaller diameter is 25 mm, the length is 51 mm.

The invention has been described with reference to examples of specific embodiments thereof. Many modifications can be carried out without thereby deviating from the scope of the invention being defined by the scope of the appended claims.

For instance, the body of the devices may have other shapes than the conical or frusto-conical, axisymmetric shapes shown in the described embodiments. Furthermore, combinations of the different embodiments may be performed as well.

What is claimed is:

1. A vaginal device for prevention of involuntary urination in a female having a vagina and a bladder, comprising a body arranged in an inserted position in the vagina, said body having a substantially elongated shape with a longitudinal axis extending, in an intended direction of insertion, from a proximal to a distal end, said body being made from a compressive and elastically deformable material and further including at least one part protruding circumferentially from an outer surface of the body, substantially perpendicular to the longitudinal axis and approximately midway therealong, providing at least one pressure area for compressive action on and support of the neck of the bladder through a vaginal wall, said pressure area preventing involuntary urination while allowing the female to urinate voluntarily with said device in said inserted position, said body also being provided with at least one string extending from the distal end.

2. A device according to claim 1, characterized in that the device is substantially symmetric with respect to the longitudinal axis of the body, preferably axisymmetric.

3. The device according to claim 2, wherein the device is substantially axisymmetric with respect to the longitudinal axis of the body.

4. The device according to claim 1, wherein the body comprises at least two protruding parts having an adjacent low part shaped as a narrowed waist between them.

5. The device according to claim 4, wherein the body comprises three protruding parts substantially perpendicular to said longitudinal axis and substantially parallel with one another, a first protruding part nearest said distal end having a first circumference, a second protruding part having a second circumference smaller than said first circumference and separated from said first protruding part by a first adjacent low part, and a third protruding part having a third circumference smaller than said second circumference, said third protruding part separated from said second protruding part by a second adjacent low part.

6. The device as set forth in claim 5, wherein said first and second adjacent low parts each have a width of at least 3 mm.

7. The device as set forth in claim 5, wherein a distance between a peak of a protruding part and a bottom of an adjacent low part is approximately 5 mm.

8. The device as set forth in claim 4, wherein said adjacent low part has a width of at least 3 mm.

9. The device according to claim 1, wherein the body is substantially conical or frusto-conical in shape.

10. A device according to claim 9, characterized in that said proximal end corresponds to the base of the conical or frusto-conical body.

11. A device according to any of the preceding claims, characterized in that the body is formed in polyurethane or polyvinyl alcohol.

12. A device according to any of claims 1 to 10, characterized in that the body is formed in a hydrophobic material, preferably hydrophobic polyurethane.

13. The device according to claim 12, wherein the hydrophobic material is a polyurethane.

14. A device according to any of the preceding claims, characterized in that the body is formed in a porous material.

15. The device according to claim 1, wherein the body is arranged in the vagina for compressive action on and support of the urethra as well as the neck of the bladder.

16. The combination of an applicator and a vaginal device for prevention of involuntary urination in a female having a vagina and a bladder, comprising a body arranged in an inserted position in the vagina, said body having a substantially elongated shape with a longitudinal axis extending, in an intended direction of insertion, from a proximal to a distal end, said body being made from a hydrophobic, compressive and elastically deformable material and being substantially conical or frusto-conical in shape with a base corresponding to said proximal end, said body further including at least two parts protruding from an outer surface of the body, separated by an adjacent low part and extending substantially parallel to the longitudinal axis of the body to provide at least one pressure area for compressive action on and support of the neck of the bladder through a vaginal wall, said body further having at least one string extending from the distal end and said applicator including an elongated member for abutment with at least said distal end of the body of the device during insertion.

17. The combination according to claim 16, characterized in that the body is provided with an indentation in said distal end; and that the applicator comprises one substantially rod-shaped end portion for abutment with said indentation.

18. The combination according to claim 17, wherein the applicator has marks for indicating the introduction depth of the applicator at its distal end.

19. The combination according to claim 16, wherein the elongated member of the applicator comprises an internal substantially tubular part which fits into an external substantially tubular part.

20. The combination according to claim 19, wherein the external substantially tubular part is open at both ends and defines a cavity for accommodating said device in a compressed and elastically deformed state.

21. The combination according to claim 19, wherein the internal substantially tubular part accommodates the device in a compressed and elastically deformed state.

22. A method of manufacturing a device according to claim 1, comprising the steps of mixing the components of the material, injecting the material into a mold, optionally accelerating hardening of the material by heating the mold, and removing the body from the mold.

23. A method according to claim 22, in which at least one string is fastened to the body at any stage of the process.

24. A method according to claim 23, in which the string is fastened to at least one portion of the mould prior to the injection of the material into said mould.

25. The combination as set forth in claim 21, wherein the applicator reduces a circumference of the device at time of insertion by at least 50%.

26. A vaginal device for prevention of involuntary urination in a female having a vagina and a bladder, comprising a body arranged in an inserted position in the vagina, said body having a substantially elongated shape with a longitudinal axis extending, in an intended direction of insertion, from a proximal to a distal end, said body being made from a compressive and elastically deformable material and including at least two protruding parts extending substantially parallel to the longitudinal axis of the body and separated by an adjacent low part, said protruding parts providing at least one pressure area for compressive action against the neck of the bladder through the vaginal wall and said low part between said two protruding parts making a cradle which fits the neck of the bladder for support, said body preventing involuntary urination while allowing the female to urinate voluntarily with said device in said inserted position, said body further being provided with at least one string extending from the distal end.

27. The device according to claim 26, wherein the device is substantially symmetric with respect to the longitudinal axis of the body.

28. The device according to claim 26, wherein the body comprises at least three protruding parts extending substantially parallel to the longitudinal axis of the body, with each protruding part separated from the others by an adjacent low part.

29. The device according to claim 28, wherein the protruding parts are spaced approximately equidistantly from one another around the circumference of the body.

30. The device according to claim 26, wherein the body is substantially conical or frusto-conical in shape.

31. The device according to claim 30, wherein the body comprises at least three protruding parts extending substantially parallel to the longitudinal axis of the body, with each protruding part separated from the others by an adjacent low part.

32. The device according to claim 31, wherein the protruding parts are spaced approximately equidistantly from one another around the circumference of the body.

33. The device as set forth in claim 31, wherein said adjacent low parts each have a width of at least 3 mm.

34. The device as set forth in claim 31, wherein a distance between a peak of a protruding part and a bottom of an adjacent low part is approximately 5 mm.

35. The device according to claim 30, wherein said proximal end corresponds to a base of the conical or frusto-conical body.

* * * * *